United States Patent [19]
Johnson

[11] Patent Number: 5,380,283
[45] Date of Patent: Jan. 10, 1995

[54] RAPID EXCHANGE TYPE DILATATION CATHETER

[75] Inventor: Kirk L. Johnson, Miami Lakes, Fla.

[73] Assignee: Cordis Corporation, Miami Lakes, Fla.

[21] Appl. No.: 155,994

[22] Filed: Nov. 22, 1993

Related U.S. Application Data

[62] Division of Ser. No. 54,430, Apr. 28, 1993, Pat. No. 5,334,147.

[51] Int. Cl.⁶ .......................................... A61M 25/00
[52] U.S. Cl. ................................... 604/96; 604/102; 604/160; 606/194
[58] Field of Search ......................... 604/95–102, 604/160, 165; 606/191, 192, 194; 128/772

[56] References Cited

U.S. PATENT DOCUMENTS

| | | | |
|---|---|---|---|
| B1 4,762,129 | 7/1991 | Bonzel. | |
| 4,748,982 | 6/1988 | Horzewski et al. | |
| 4,762,129 | 8/1988 | Bonzel. | |
| 5,040,548 | 8/1991 | Yock. | |
| 5,063,018 | 11/1991 | Fontirroch et al. | |
| 5,135,535 | 8/1992 | Kramer | 606/194 |
| 5,154,725 | 10/1992 | Leopold. | |
| 5,171,222 | 12/1992 | Euteneuer et al. | 604/102 |
| 5,205,822 | 4/1993 | Johnson et al. | |
| 5,263,932 | 11/1993 | Jang | 604/96 |
| 5,267,958 | 12/1993 | Buchbinder et al. | 606/194 |

*Primary Examiner*—C. Fred Rosenbaum
*Assistant Examiner*—Chalin Smith
*Attorney, Agent, or Firm*—Gerstman, Ellis & McMillin, Ltd.

[57] ABSTRACT

A balloon dilatation catheter defines an inflation lumen communicating with its balloon, and a guidewire lumen extending along the catheter. An aperture portion is defined in the catheter shaft between the guidewire lumen and the catheter exterior, the aperture portion being covered by a frangible wall that is typically thinner than the rest of the tubular catheter shaft wall. The catheter may be used in either the conventional over-the-wire technique or the "rapid exchange" technique of balloon angioplasty.

16 Claims, 1 Drawing Sheet

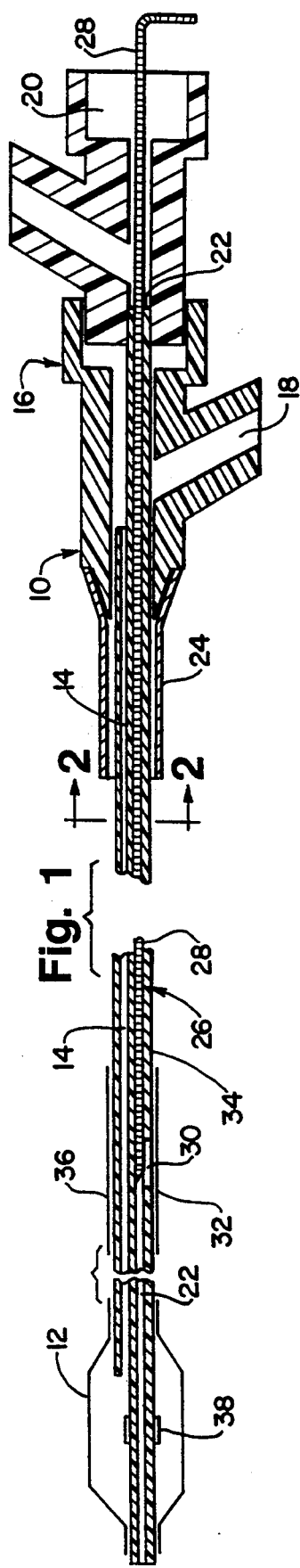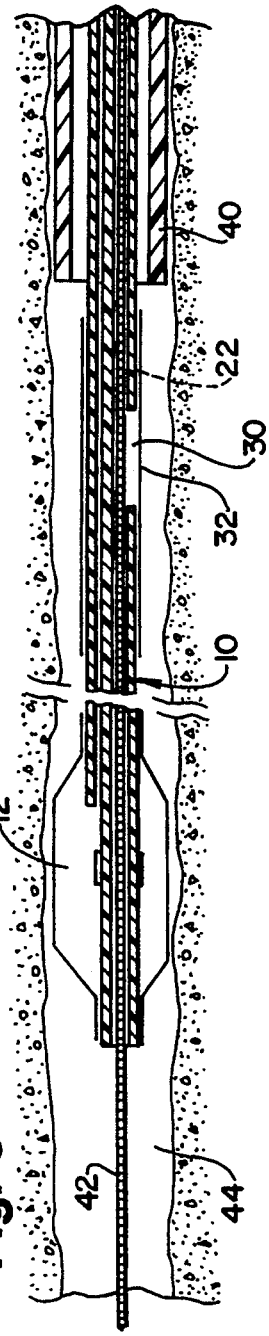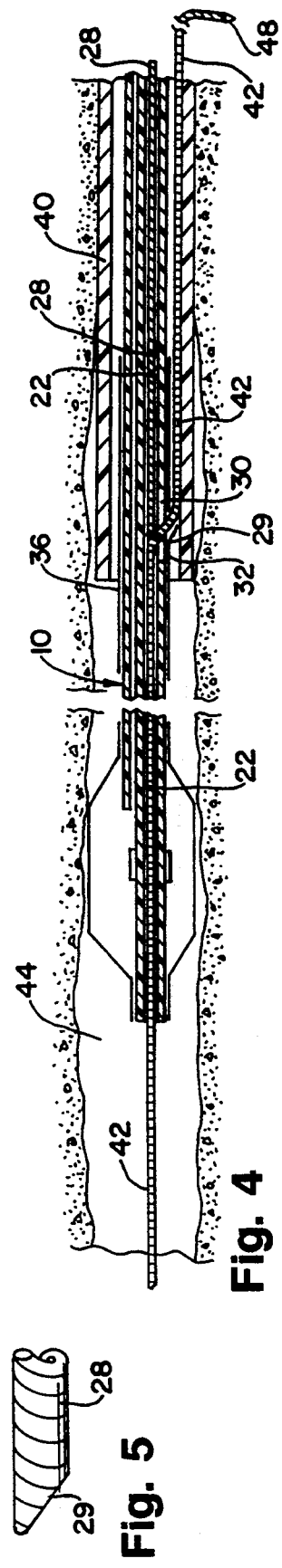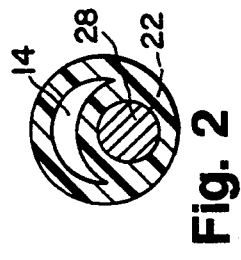

RAPID EXCHANGE TYPE DILATATION CATHETER

This is a division of application Ser. No. 08/054,430, filed Apr. 28, 1993 now U.S. Pat. No. 5,334,147.

BACKGROUND OF THE INVENTION

"Rapid Exchange"-type balloon dilatation catheters are catheters which are capable of advancement into the vascular system of a patient along a pre-emplaced guidewire for balloon angioplasty or the like, in which the guidewire occupies a lumen of the catheter in only a distal portion thereof. With respect to the catheter proximal portion, the guidewire exits from the internal catheter lumen and extends along the side of the catheter, being typically retained in that position by a guiding catheter in which both the catheter and the guidewire are contained. Examples of catheters of this general type include those disclosed in Horzewski et al. U.S. Pat. No. 4,748,982; Bonzel U.S. Pat. No. 4,762,129; and Yock U.S. Pat. No. 5,040,548.

In the catheters of the above-cited patents, the distal guidewire lumens of the catheters shown have an aperture through which the guidewire can extend, so that in portions of the catheter proximal thereto the guidewire is outside of the catheter, running essentially parallel to it. By this means, the use of a guidewire extension can be avoided when exchanging catheters, providing a more rapid exchange.

A disadvantage of "rapid exchange" type catheter systems having a lateral aperture is that the guidewire cannot be removed and exchanged while the catheter is indwelling in the patient. Furthermore, the reduced length of engagement between the guidewire and catheter can compromise the handling characteristics of the catheter. Likewise, the guidewire lumen of such catheters cannot be flushed with fluids to clear out obstructions and the like, since the patent guidewire lumen is not in fluid communication with the proximal catheter hub.

The conventional, over-the-wire mode of catheter administration lacks these disadvantages, but presents the user a different and substantial disadvantage in that, typically, it becomes necessary to attach a catheter extension wire to the proximal end of the guidewire in order to exchange catheters without moving the guidewire out of-position in the patient. However as an advantage of the over-the-wire mode, the guidewire may be quickly and easily removed and replaced without moving the catheter that surrounds it out of position. In the typical "rapid exchange" type of catheter, the guidewire usually cannot be replaced while retaining the catheter in position.

By this inventions, a catheter is provided which is capable of use in the normal, over-the-wire mode of surgical use of conventional catheters that lack any side aperture or slit, to achieve the known advantages of that system. However, if it becomes desirable to use the catheter of this invention in the "rapid exchange" mode of operation, to gain those advantages, that can also be accomplished.

DESCRIPTION OF THE INVENTION

By this invention, a balloon dilatation catheter is provided having proximal and distal ends. The catheter comprises a flexible, tubular wall defining a catheter shaft, which shaft typically carries a dilatation balloon adjacent the distal catheter end. The catheter shaft typically defines an inflation lumen communicating with the balloon, plus a guidewire lumen which is separate from the inflation lumen and which extends substantially the length of the catheter and through the catheter distal end.

By this invention, a side opening aperture portion is defined in the catheter shaft, which aperture portion communicates between the guidewire lumen and the catheter exterior. The aperture portion is covered by a frangible wall. Thus, in use, one may pass the proximal end of a guidewire that is typically emplaced in the vascular system of the patient into the distal end of the guidewire lumen of the catheter of this invention. One may advance the catheter distally along the guidewire, including the step of puncturing a side opening aperture portion in the catheter by breaking the frangible wall, and causing the guidewire proximal end to pass through the side opening aperture portion, so that a proximal portion of the guidewire can lie outside of and alongside the advancing catheter as the catheter is advanced. Thus the guidewire may be grasped near its proximal end as the catheter is advanced, so that the catheter may be so advanced into a patient along the emplaced guidewire without the need of a guidewire extension being attached to the guidewire proximal end.

If desired in the above process, the side opening through the frangible wall may be punctured by the proximal end of the guidewire, which may carry an appropriate puncturing point for that purpose. Otherwise, the frangible wall may be opened by a scalpel or the like.

Thus, the catheter of this invention may be initially intended for use as a standard over-the-wire catheter in conventional balloon angioplasty such as PTCA. Then, for any reason, the surgeon may change his mind and make use of the catheter's capability in operation in accordance with a "rapid exchange" technique, as described above herein.

Preferably, a proximal portion of the guidewire lumen of the catheter of this invention carries a support mandrel, the remainder of the guidewire lumen being unoccupied. This facilitates the use of the catheter in the "rapid exchange" mode of operation for stiffening of the catheter. However, it is preferred for the support mandrel to be removable, so that the catheter may also be used in the conventional, over-the-wire mode. Because the catheter of this invention is initially sealed along its entire, lateral extent, it is possible to pass pressurized fluids through the guidewire lumen for flushing and the like, prior to puncturing of the frangible wall at the aperture portion. Preferably, the support mandrel, when present, extends distally to essentially the aperture portion. The support mandrel may have a tapered tip, which can be positioned to serve as a guide to assist in urging the guidewire out of the aperture portion.

The frangible wall described above may be part of a tubular sleeve surrounding the catheter, with the frangible wall being that portion of the sleeve overlying the aperture portion, being typically thinner than the catheter wall, to be more frangible than the catheter wall by that or any other means. Alternatively, other forms of the frangible wall may be used, including integral, frangible wall portions made from the material of the catheter tubing itself.

The catheter of this invention is typically passed through a guiding catheter, especially in the "rapid exchange" mode of operation, to assure that the portion of the guidewire which passes through the side opening aperture portion as the catheter is advanced extends proximally from the side opening and generally parallel to the catheter, being held in close relationship therewith by the guiding catheter.

DESCRIPTION OF DRAWINGS

In the drawings, FIG. 1 is a longitudinal, sectional view of a catheter in accordance with this invention;

FIG. 2 is an enlarged, sectional view taken along line 2—2 of FIG. 1;

FIG. 3 is a sectional view of the distal portion of the catheter of FIG. 1 within an artery, showing the catheter being advanced along a guidewire in accordance with the conventional, over-the-wire mode;

FIG. 4 is a longitudinal sectional view of the same catheter in an artery, showing the catheter being advanced in accordance with the "rapid exchange" mode; and FIG. 5 is a fragmentary, elevational view of the distal tip of the removable mandrel.

DESCRIPTION OF PREFERRED EMBODIMENT

Referring to the drawings, the proximal and distal portions of catheter 10 are shown in accordance with this invention. Catheter 10 is designed for balloon angioplasty having a typical length of about 140 centimeters and a conventional diameter to permit entry into the small branches of the coronary arteries, for angioplasty by inflation of balloon 12 through inflation lumen 14. Lumen 14 extends from balloon 12 through a conventional hub 16. Hub 16 has a connection 18 with the inflation lumen, and a second connection 20 with a separate guidewire lumen 22, which extends the entire length of the catheter. Strain relief 24 is provided to assist in strong securance of hub 16 to the catheter body 26.

Removable mandrel 28 is positioned in a proximal portion of the guidewire lumen. Mandrel 28 is provided for stiffening a proximal portion of the catheter during insertion in accordance with the "rapid exchange" mode. Mandrel 28 may be removed if the catheter is to be used in the over-the-wire advancement mode.

The components of catheter 10 may be typically of conventional design except as otherwise described herein.

In accordance with this invention, catheter body 26 defines aperture portion 30, said aperture portion being defined to communicate through the catheter wall from the guidewire lumen 22 to the exterior, except that aperture portion 30 is covered by a frangible wall 32, which is thinner than the tubular catheter shaft wall 34. Frangible wall 32 may be part of a thin-walled plastic tube 36 which is sealed to the catheter body 26 in a position to cover aperture 30 portion. Aperture portion 30 is typically located about 20 or 30 cm. proximal to balloon 12, for example 28 cm.

Mandrel 28 defines a tapered tip 29 to assist in urging guidewire 42 out of aperture portion 30 when that is desired.

Catheter 10 may also carry an x-ray visible marker band 38 to indicate the position of balloon 12 on a fluoroscope.

FIG. 2 shows a cross-section of the respective catheter lumens 14, 22, the specific design being as shown in Fontirroche et al. U.S. Pat. No. 5,063,018.

Referring to FIG. 3, the distal end of catheter 10 of FIG. 1 is shown projecting out of the distal end of a conventional guiding catheter 40 which, in turn, has been emplaced, along with a guidewire 42, in a coronary artery 44. As shown in FIG. 3, a distal portion of catheter 10, is projecting outwardly from guiding catheter 40, with guidewire 42 extending through the entire length of catheter 10, support mandrel 28 having been removed.

In such a configuration, catheter 10 is functioning in the conventional, over-the-wire manner. Frangible wall 32 remains unbroken so that the guidewire lumen 22 is intact from end to end without an open side aperture.

However, when so desired, the same catheter of this invention may be used in the "rapid exchange" mode as shown in FIG. 4. In this embodiment, catheter 10 is shown being advanced forwardly out of guiding catheter 40 into coronary artery 44. However, in this embodiment, as catheter 10 is advanced along the guidewire 42 with guidewire 42 occupying guidewire lumen 22, frangible wall 32 was broken, either with a pointed, reinforced end 48 of the guidewire 42, or by use of a scalpel or other tool to puncture frangible wall 32, so that guidewire 42 may pass through aperture portion 30, as shown, urged by bevelled tip 29 if desired. Guidewire 42 passes out of aperture portion 30, and then extends proximally from aperture 30 on the outside of catheter 10. Typically most of that proximal portion of guidewire 22 is constrained within the bore of guiding catheter 40. The remainder of guidewire lumen 22 is thus not occupied by guidewire 42, but is preferably occupied by removable mandrel 28 in order to stiffen the catheter.

By this means, the advantages of the "rapid exchange" catheter can be achieved where that is desired, particularly the emplacement and withdrawal of catheter 10 without the need for a guidewire extension. However, if desired, the same catheter may be used in conventional, over-the-wire manner, permitting pressurized fluids to pass from end to end of guidewire lumen 22 and other advantages in those circumstances where that is desired. Catheter 10, balloon 12, and the sleeve 36 which defines frangible wall 32 may be made of conventional plastic materials such as nylon or polyethylene terephthalate.

The above has been offered for illustrative purposes only and is not intended to limit the scope of the invention, which is as defined in the claims below.

That which is claimed is:

1. A method of inserting a balloon dilatation catheter into the vascular system of a patient along a guidewire previously emplaced in the patient, which comprises:
passing the proximal end of the guidewire into the distal end of a guidewire lumen of the catheter, and advancing the catheter distally along the guidewire; puncturing a side opening in said catheter through a catheter wall portion that is thinner than most of the catheter wall, said punctured side opening extending between the guidewire lumen and the exterior of the catheter; and causing the guidewire proximal end to pass through said side opening from the guidewire lumen to the exterior as the catheter is advanced.

2. The method of claim 1 in which a portion of said guidewire passes through said side opening as the catheter is advanced, and said portion extends proximally from said side opening and generally parallel to said catheter.

3. The method of claim 2 in which said side opening is punctured at a position spaced proximally of the balloon of said catheter.

4. The method of claim 3 in which a support mandrel is placed in a proximal portion of said guidewire lumen spaced from said side opening.

5. The method of claim 1 in which said side opening is punctured by the proximal end of said guidewire.

6. The method of claim 1 in which a portion of said guidewire passes through said side opening as the catheter is advanced, and said portion extends proximally from said side opening and generally parallel to said catheter while a support mandrel is positioned in a proximal portion of said guidewire lumen spaced from said side opening, said opening being punctured at a position spaced proximally of a balloon of said catheter.

7. The method of claim 6 including the step of puncturing said side opening with the proximal end of said guidewire.

8. A method of inserting a balloon dilatation catheter into the vascular system of a patient along a guidewire previously emplaced in the patient, which comprises:
passing the proximal end of the guidewire into the distal end of a guidewire lumen of the catheter, and advancing the catheter distally along the guidewire; puncturing a side opening in said catheter between the guidewire lumen and the exterior of the catheter; and causing the guidewire proximal end to pass through said side opening from the guidewire lumen to the exterior as the catheter is advanced, in which a portion of said guidewire which passes through said side opening as the catheter is advanced extends proximally from said side opening and generally parallel to said catheter while a support mandrel is positioned in a proximal portion of said guidewire lumen spaced from said side opening, said opening being punctured at a position spaced proximally of a balloon of said catheter.

9. The method of claim 8 including the step of puncturing said side opening with a proximal end of said guidewire.

10. The method of claim 3 in which said support mandrel has a tapered distal tip, said support mandrel distal tip being positioned to urge the guidewire proximal end out of said side opening as the catheter is advanced over the guidewire.

11. The method of inserting a balloon dilation catheter into the vascular system of a patient along a guidewire previously emplaced in the patient, which comprises:
passing the proximal end of the guidewire into the distal end of a guidewire lumen of the catheter, and advancing the catheter distally along the guidewire; puncturing a side opening in said catheter between the guidewire lumen and the exterior of the catheter, using the proximal end of said catheter; and causing the guidewire proximal end to pass through said side opening from the guidewire lumen to the exterior as the catheter is advanced.

12. The method of claim 11 in which said side opening is punctured at a position spaced proximally of the balloon of said catheter.

13. The method of claim 12 in which a support mandrel is positioned in a proximal portion of said guidewire lumen spaced from said side opening as said side opening is punctured by the proximal end of said guidewire.

14. The method of claim 13 in which said support mandrel has a tapered distal tip, said support mandrel distal tip being positioned to urge the guidewire proximal end out of said side opening as the catheter is advanced over the guidewire.

15. The method of claim 1 in which a support mandrel is placed in a proximal portion of said guidewire lumen spaced from said side opening.

16. The method of claim 1 in which said support mandrel has a tapered distal tip, said support mandrel distal tip being positioned to urge the guidewire proximal end out of said side opening as the catheter is advanced over the guidewire.

* * * * *